United States Patent [19]
Bardinelli et al.

[11] Patent Number: 5,989,429
[45] Date of Patent: Nov. 23, 1999

[54] PROCESSES FOR FORMING STABILIZED LIQUID BIOCHEMICAL AGRICULTURAL PRODUCTS

[75] Inventors: Ted R. Bardinelli, Durham; David E. Mann, Fuquay-Varina; David G. Hobbs, Raleigh, all of N.C.

[73] Assignee: KHH Biosci, Inc., Research Triangle Park, N.C.

[21] Appl. No.: 08/995,980

[22] Filed: Dec. 22, 1997

[51] Int. Cl.$^6$ .......................... B01D 11/00; B01D 11/02; B01D 11/08; A01N 65/00
[52] U.S. Cl. .................................. 210/634; 71/11; 71/23; 210/639; 210/774; 210/806; 424/195.1
[58] Field of Search ............................ 424/195.1, 195.11; 71/11, 23; 210/634, 638, 774, 805, 806, 639; 159/47.1, 47.2; 203/50

[56] References Cited

U.S. PATENT DOCUMENTS

| | | | |
|---|---|---|---|
| 2,046,181 | 6/1936 | Remy | 424/195.1 |
| 2,983,724 | 5/1961 | Pearl | 424/195.1 |
| 3,415,928 | 12/1968 | Nadal | 424/195.1 |
| 4,552,666 | 11/1985 | Muller | 71/23 |
| 4,666,498 | 5/1987 | Muller | 71/23 |
| 4,863,734 | 9/1989 | Pommer et al. | 424/195.1 |
| 5,837,253 | 11/1998 | Cohen | 424/195.1 |

OTHER PUBLICATIONS

"Investigations about the Occurence and Chemical Nature of the Resistance Inducing Factor in the Extract of *Reynoitria sachalinensis*" Biological Bundesantalt, Med. Fac Landbouww. Univ. Gent 57/2b 1992, Kowaewlski et al.

"Ocena Fungicydalnego Dzialania Wyciagow Roslinnych N.Grzyby Powodujace ZGOrzel Siewek buraka", Biuletyn Instytutu Hodowli I Aklimatyzaoji Roslin, Piotrowska et al, 1997, pp. 253–258.

*Primary Examiner*—Joseph W. Drodge
*Attorney, Agent, or Firm*—Nixon & Vanderhye P.C.

[57] ABSTRACT

Processes for forming a stabilized liquid biochemical agricultural product containing an organic solvent extract of Reynoutria sachalinensis comprising subjecting an organic solvent extract of dried particulate *Reynoutria sachalinensis* to first and second extract concentration stages, and wherein prior to said second extract concentration stage, the concentrated extract from said first extract concentration stage is mixed with a liquid stabilizer, most preferably a liquid nitrogen-containing fertilizer.

23 Claims, No Drawings

PROCESSES FOR FORMING STABILIZED LIQUID BIOCHEMICAL AGRICULTURAL PRODUCTS

FIELD OF THE INVENTION

The present invention relates generally to the production of biochemical agricultural products. In preferred embodiments, the present invention relates to processes for forming a concentrated extract of the plant *Reynoutria sachalinensis* and to the resulting biologically active product.

BACKGROUND AND SUMMARY OF THE INVENTION

The plant *Reynoutria sachalinensis* (commonly known as "giant knotweed", and hereinafter more simply referred to as "Reysa") is known to possess agricultural fungicidal activity as evidenced from U.S. Pat. No. 4,863,734 to Pommer et al (the entire content of which is expressly incorporated hereinto by reference). In this regard, it is known that Reysa may be extracted with an organic solvent, such as ethanol, and then subjected to partial evaporation of the ethanol so as to obtain an ethanol extract of Reysa. However, several problems exist when extracting Reysa (or other plant materials) with an organic solvent.

In this regard, when plant materials are extracted with an organic solvent, such as ethanol, the resulting extract includes a complex mixture of materials which vary in terms of water solubilities. The extraction of plant materials can, and often does, result in extracts containing chlorophyll, waxes and oils in addition to more water soluble components. The less water soluble components separate and agglomerate (so-called "tarring out") upon removal of the organic solvent. The extracts and concentrates can also be susceptible to microbial decomposition once the ethanol is removed, thereby leading to inefficacious results.

Broadly, the present invention is embodied in processes to form stable formulations of solvent-extracted Reysa containing minimal (if any) residual organic solvent and to the stable formulations thereby obtained. In particular, the present invention involves subjecting an alcoholic Reysa extract to a primary concentration step (e.g., via distillation, evaporation or the like) to remove a major portion of the organic solvent and to concentrate the Reysa in the resulting primary concentrate solution. Thereafter, an inorganic or organic (e.g., urea) liquid stabilizer is added to the primary concentrate solution which is thereafter subjected to a secondary concentration step so as to remove substantially all (e.g., greater than 95 wt. %) of the organic solvent. In such a manner, therefore, Reysa formulations are provided which are stabilized against microbial decomposition and the resulting reduced inefficacy.

DETAILED DESCRIPTION OF THE INVENTION

The plant *Reynoutria sachalinensis* ("Reysa") that may be used in the practice of the present invention includes not only the plant itself, but also plant parts such as the rhizome, stem, leaves or a blend thereof. Preferably, the dead Reysa plant, especially dried, is used. It is particularly preferred that the plant and/or plant parts are initially air dried or dried with the gentle application of heat following which they are pulverized to form a particulate Reysa powder. Particularly, field grown Reysa plants may be harvested, dried to a maximum of about 15% moisture content, and then milled to a coarse flake using a shredder.

The dried Reysa flakes may then be subjected to organic solvent extraction using techniques well known to those skilled in this art. Most preferably, the organic solvent employed for extracting the active ingredient(s) of Reysa is ethanol or denatured alcohol (ethyl). Preferably, at least about 0.5 liter of ethanol per kilogram (L/kg) of Reysa is employed, and more preferably at least about 0.75 L/kg. Particularly effective results are obtained, however, if a significant excess of ethanol is employed, for example, up to about 6 liters of ethanol per kilogram of Reysa. This establishes the ratio of solvent to Rs and the minimum recommended extraction time for the "tea method" of extraction. Typically, denatured ethanol is used due to cost, pure ethanol is preferred but not necessary. Care should be taken, however, that the denaturing agents are not phytotoxic if concentrated in the final product. Normally, such denaturing agents are extracted with the ethanol in the distillation phase of this process. Extraction may be carried out under agitation conditions at room temperatures. Soxhlet extraction is also suitable.

The liquid ethanol Reysa extract is subsequently separated from the particulate plant material by filtration (e.g., using a filter bag with 250 micron pore size filtration medium) and transferred to a distillation vessel. The particulate plant material that remains after filtration may then be subjected to a second stage extraction with fresh ethanol. Again, it is preferred that an excess of ethanol be employed, that is, up to about 6 L/kg.

The second stage liquid ethanol Reysa extract is separated from the dried plant material and preferably combined with the liquid extract from the first stage extraction in the distillation vessel. The exhausted particulate plant material will contain some residual ethanol may then be stripped to recover ethanol or washed with water and discarded. Additional extract might be recovered using a centrifuge, a filter press or compactor. Additional extract might also be recovered by steam stripping, direct heat distillation, vacuum distillation of Rs solids retaining ethanol.

The combined ethanol Reysa extracts from the first and second stage ethanol extractions may then be subjected to a first stage distillation procedure using conventional distillation techniques so as to remove a major portion of the ethanol as distillate and concentrate the amount of Reysa extract in the bottoms. In this regard, the first stage distillation is most preferably carried out so that at least about 60 vol. %, and more preferably at least about 70 vol. %, of the ethanol is distilled away from the Reysa extract. First stage distillation is most preferably accomplished under nitrogen for safety reasons. Typically, the distillation vessel is composed of stainless steel jacketed vessel, steam heated and capable of withstanding vacuum. The attached condenser column is cooled by a glycol based fluid kept below 40° F. to allow vacuum distillation (which is faster and less destructive than distillation at 76° C.).

Following first stage distillation, the concentrated Reysa extract (containing no more than about 40 vol. % ethanol, and more preferably no more than about 30 vol. % ethanol) is mixed with a liquid stabilizer. This step is performed after the minimum practical volume is achieved in the distillation vessel which is determined by the vessel configuration as well as the fluid nature of the distillate residue (bottoms).

Virtually any liquid stabilizer that is biologically compatible with the Reysa extract and has a boiling point that is significantly (i.e., at least about 10° C.) greater than the boiling point of the organic solvent (e.g., ethanol) may be employed in the practice of this invention. Most preferably, the liquid stabilizer is one that has some biological benefit. Specifically, it is preferred that the liquid stabilizer is a liquid nitrogen-containing fertilizer.

One liquid fertilizer that may be employed successfully in the practice of this invention is a salt solution containing at least one nitrogen-containing compound selected from urea, ammonium nitrate, calcium nitrate and magnesium chloride at concentrations between 15 to about 60% (w/v), and more preferably between about 20 to about 40% (w/v). A preferred liquid fertilizer is a salt solution of urea (25% w/v) with at least one of ammonium nitrate (about 18% w/v), calcium nitrate (about 20 w/v %) and magnesium chloride (about 10% w/v). A particularly preferred liquid fertilizer is commercially available from BASF Corporation under the registered trademark BASFoliar® 36 fertilizer.

Distillation is further continued so as to remove a major portion of the remaining ethanol to a maximum of about 5% w/w residual concentration. The amount/weigh of the distillate residue just prior to addition of the liquid stabilizer, less the solids content of the distillate residue, is the target for the additional distillation volume in this process step. The product is then cooled and mixed with a high shear agitator (e.g., for up to about 30 minutes), filtered (to less than 100 microns) and packaged for use.

Although one particularly preferred technique has been discussed above to extract Rs solids with ethanol, those skilled in the art will recognize that numerous equivalent extraction techniques may be employed in the successful practice of this invention. For example, one may use counter current solvent extraction using a series of baskets holding Rs solids that are percolated with solvent as they progress through the extractor (e.g., via a Crown Extractor). Filter presses may alternatively be loaded with Rs solids through which a solvent is passed (e.g., the "tea bag" technique) or a Buchner filter may be loaded with Rs solids and washed with solvent. Furthermore, it is entirely possible that Soxhlet extraction may cycle distilled solvent through the Rs solids held in a filer basket wherein the extract is collected in a boiling vessel that provides solvent vapors to the condenser above.

Tall tubes fitted with, for example 10 US mesh filter plates, a fluid collection space and a valve on the bottom may be filled with Rs solids. Solvent may then be recycled from top to bottom until saturation is achieved. This process is repeated until the Rs is depleted. A piston may then be used to press the Rs solids so as to squeeze retained solvent therefrom and, finally, to push out the depleted Rs solids when the bottom plate is removed.

One extraction technique that could be employed so as to eliminate distillation is to spray dry the extracted solids in the presence of an inert carrier to form a free flowing powder that can be suspended in an aqueous spray solution for foliar application.

EXAMPLES

Further understanding of this invention will become evident from the following non-limiting Examples.

Example I

Batch Preparation of Reysa Formulations

One drum (370 lbs.) of C-95 denatured ethanol (ChemCentral Co.) was added to a three drum stainless steel round bottom mixing kettle and 82.75 lbs. of dried and crushed Reysa was added with agitation. After three hours of agitation, the mixture was drained through a 250 micron filter bag, leaving the plant material in the kettle. 224.5 lbs. of an ethanoic extract (E1) was then passed through a 100 micron filter bag (1.52% solids by gravametric analysis) and into a distillation vessel. Filtration required one hour.

A drum of ethanol (370 lbs.) was added to the mixing kettle and 87.2 lbs. of dried and crushed Reysa was added. After three hours of agitation, recovery was initiated via a 250 micron filter. The 268 lbs., or 72.4% recovery, extract (E3) was transferred to the distillation vessel (a 100 gallon, steam heated, stainless steel vessel with condenser) for solvent recovery. Filtration took 45 minutes.

Another drum of ethanol (370 lbs.) was added to the Reysa remaining in the mixing kettle and after a short period of agitation, was allowed to stand overnight without agitation. While the second extraction (E2) was being filtered, the first extraction (E1) was vacuum distilled (−22 inches Hg) in the distillation vessel at a temperature of 30°–38° C. to achieve 13.93% solids content by weight. Extraction E2 yielded 274 lbs. of extract (0.72% solids) which was filtered via a 100 micron filter into the distillation vessel combined with tailings from E1 distillation thereby realizing a loss of 241.5 lbs. of ethanol, equal to about 33% of the original ethanol charge due to absorption by the plant material.

Reysa plant residues from the first two extractions were suspended in water and filtered to remove excess ethanol. The filtrate and exhausted Reysa plant material was discarded. The wash process took one hour.

Another drum of ethanol was added to the Reysa material in the mixing kettle, agitated and let stand overnight. Filtration in the morning took one hour. The resulting extract (E4) had a solids content of 0.63% and a total weight of 357 lbs. (99% recovery). Extracts E3 and E4 were combined in the distillation vessel and sampled yielding 625 lbs. net weight (at 0.87% solids by weight). The combined extracts were then distilled at 47° C. and 20 inches Hg. Approximately 100 lbs. distillate was removed every 30 minutes. The distillation of combined extracts E3 and E4 continued for two hours to a final weight of 141 lbs. (484 lbs. distillate).

Meanwhile, extracts E1 and E2 were distilled, collecting 360 lbs of distillate from 490 lbs of extract, a 73% weight reduction. Temperature began at 60° C. and fell to 35° C. when the 22 inches Hg of vacuum was applied and the extract boiled. E1 and E2 tailings totaled 24 lbs. and contained 26.11 % solids.

The distillate from combined extracts E1 and E2 (360 lbs) was added to Reysa residue from extract E4 and agitated for 2.5 hours. The 362 lbs (100% recovery) E5 extract was recovered, sampled (0.28% solids) and added to E3 and E4 extract residues in kettle #19. Net weight was 510 lbs. at the restart of distillation. Two hours of distillation at 46°, 22 inches Hg, brought the net weight in kettle #19 to 91 lbs. which had 6.5% (5.9 lbs.) solids.

The tailings from E1 through E5 were combined in kettle #1 to yield 12.04% solids. Vacuum distillation removed 51.5 lbs of ethanol and then the product was cooled to room temperature overnight.

BASFoliar® Extra liquid fertilizer (BASF Corporation) was added in an amount of 11.14 lbs/gal to kettle #1 in two charges: 55.8 lbs+55.0 lbs.=110.8 lbs=37.65 Liters (0.5 Liters liquid fertilizer per kg of Reysa extracted). Vacuum distillation then continued until a total of 85 lbs distillate had been collected over a period of two hours. Temperatures ranged from 40° C. to 56° C. at 25 inches Hg.

Based on distillate weights, the theoretical final weight was 140 lbs, based on solids content, the theoretical final weight would be 124 lbs. Actual collected weight for the final product sample (designation BASF 114 UBF) was, however, 102.5 lbs. Evidently some of the formulation water had been distilled off and there were transfer losses since the liquid fertilizer charge was 110 lbs and there were approximately 10–13 lbs of extracted solids.

Example II
Efficacy of Formulation on Greenhouse Ornamentals

Greenhouse trials were conducted to determine the efficacy of the Reysa formulation of Example I (BASF 114 UBF) for the control of powdery mildew diseases on a variety of ornamental crops. Tests were concentrated on roses with additional tests on poinsettia, Begonia, Gerber daisy and Salvia. The test material was applied every 7–9 days on a protectant schedule with sufficient water volume for thorough coverage. These trials were conducted under high disease pressure that generally does not exist in commercial greenhouses.

As shown in Table 1 below, the efficacy of BAS 114 UBF in accordance with the present invention was similar to that of both commercially available triadimefon (STRIKE® triadimefon commercially available from Bayer Corporation) and piperalin (PIPRON® piperalin commercially available from SePro Corporation). In addition, the efficacy of BAS 114 UBF in accordance with this invention showed similar efficacy to an ethanol extract (BAS 114 OOS) prepared by a reflux extraction using a mixture of ethanol and water (70/30) giving a final product (0.67 Reysa equiv./ml) containing 22% ethanol used at a rate of 1.5% v/v.

TABLE 1

| Treatment | Rate (%) | % Mildew Severity | |
|---|---|---|---|
| | | Trial No. 1 | Trial No. 2 |
| Untreated | — | 82 | 33 |
| BAS 114 UBF | 1.0 | 28 | 22 |
| " | 0.5 | 33 | 19 |
| " | 0.25 | 35 | — |
| BAS 114 OOS (Comparative) | 1.5 | 25 | — |
| Piperalin | 0.5 pt/100 gal | 23 | — |
| Triadimefon | 2.0 oz/100 gal | — | 19 |

Example III
Efficacy of Formulation on Cucurbits

Tests for the control of powdery mildew were conducted on cucumber, squash, melon and pumpkin. The test material was applied every 7–9 days on a protectant schedule for a total of 4–6 applications. The formulation in accordance with the present invention produced in accordance with Example I above (BAS 114 UBF) was compared against a Reysa formulation (BAS 114 UAF+) consisting of air-milled Reysa powder tank mixed with BASFoliar® liquid fertilizer (0.5% vol/vol). Other trials assessed the efficacy of BAS 114 UBF in accordance with the present invention alone and in alternation with a reduced rate of conventional fungicide (BAS 490 02F CYGNUS® fungicide commercially available from BASF Corporation) against cucumber and squash powdery mildew. The Reysa formulations were generally applied as a preventative spray on a 7 day schedule.

The results appear in Tables 2 and 3 below. The data show that, under conditions of low disease pressure (1 trial), both Reysa formulations provided excellent control of mildew, similar to the commercial standard, triadimefon (BAYLETON® fungicide commercially available from Bayer Corporation). In other trials (3 trials), where there was high disease pressure, both Reysa formulations averaged 60% disease control, but triadimefon was superior (77%). Alternating BAS 114 UBF with ½ rates of BAS 490 02F on a weekly spray interval provided excellent disease control that was similar to the full rate of BAS 490 02F. This effect was observed under low and high disease pressure conditions and demonstrates the usefulness of Reysa formulations to reduce the usage of conventional fungicides in an integrated pest management program. Phototoxicity was not observed from any of the Reysa formulations.

TABLE 2

Control of Cucurbit Powdery Mildew

| | | Avg. % Mildew Severity | | |
|---|---|---|---|---|
| Treatment | Rate[1] | Low Disease Pressure (n = 1) | High Disease Pressure (n = 3) | All Trials (n = 4) |
| Untreated | — | 23.5 | 70.4 | 58.7 |
| BAS 114 UBF | 0.5 V | 2.8 | 27.3 | 17.5 |
| BAS 114 UBF | 0.25 V | 6.3 | 34.4 | 27.4 |
| BAS 114 UAF+ | 0.25 W | 5.5 | 28.0 | 22.4 |
| BAS 114 UAF+ | 0.13 W | 7.3 | 42.5 | 33.7 |
| Bayleton | 0.10 A | 1.0 | 16.4 | 12.6 |

[1]V = % vol/vol.,
W - % wt./vol.,
A - lb ai/acre

TABLE 3

Control of Cucurbit Powdery Mildew Using Invention Formula Alone And Integrated with Conventional Fungicide Program

| | | | Avg. % Mildew Severity | |
|---|---|---|---|---|
| Treatment | Rate (% or lb ai/A) | Spray Interval (Days) | Trial No. 1 (n = 1) | Trial No. 2 (n = 3) |
| Untreated | — | — | 20.0 | 39.6 |
| BAS 114 UBF | 0.50% | 7 | 5.3 | 20.3 |
| BAS 490 02F | 0.05 lb | 14 | 5.5 | 7.2 |
| BAS 490 02F | 0.10 lb | 14 | 0.8 | 5.0 |
| Alternating[1] | (see note 1) | 7 | 1.0 | 2.1 |
| Bayleton | 0.25 | 7 | 0.0 | — |

[1]0.05 lb of BAS 490 02F alternated with 0.5% BAS 114 UBF

Example IV
Efficacy of Formulation on Grapes

BAS 114 UBF was tested for its efficacy to control powdery mildew on Red Flame and Chardonnay varieties of grapes under severe and moderate disease pressures, respectively. By way of comparison, trials were also separately conducted using sprayable sulfur, a mixture of dry milled Reysa with BASFoliar® liquid fertilizer (BAS 114 UAF+), and integrating the application of BAS 114 UBF together with myclobutanil (RALLY® myclobutanil commercially available from Rohm and Haas Co.). The results appear in Table 4 below.

As can be seen from the data, BAS 114 UBF (0.5%) provided berry powdery mildew control equal or superior to sprayable sulfur and slightly less than myclobutanil, when applied on a 7-day spray schedule. BAS 114 UAF+(0.5%+ 0.5%) was less efficacious than BAS 114 UBF (0.5%).

Weekly applications of BAS 114 UBF (0.5% before berry sizing, followed by three myclobutanil (0.045 lb. ai/acre) applications during sizing and BAS 114 UBF for the remainder of the season provided good berry powdery mildew control. The level of control was similar to that of sulfur used instead of BAS 114 UBF in the sequence. Both of these treatments were superior to myclobutanil (0.075 lb ai/acre) alone applied on a 14 day schedule.

TABLE 4

| | | | % Mildew Severity[1] | | | |
|---|---|---|---|---|---|---|
| | Rate | | Chardonnay | | Red Flame | |
| Treatment | (g ai/ha or %) | Schedule | Leaves | Berries | Leaves | Berries |
| Untreated | — | — | 21.0 | 35.0 | 30.0 | 91.0 |
| BAS 114 UBF | 0.5% | 7-day | 0.3 | 6.0 | 2.7 | 16.0 |
| BAS 114 UBF | 0.25% | 7-day | 3.0 | 17.0 | 4.3 | 37.0 |
| BAS 114 UAF+ | 0.5% + 0.5% | 7-day | 1.0 | 15.0 | 1.0 | 23.0 |
| BAS 114 UAF+ | 0.25% + 0.5% | 7-day | 6.0 | 16.0 | 1.3 | 28.0 |
| Sulfur 80WP | 5600 | 7-day | 5.0 | 8.0 | 1.3 | 29.0 |
| BAS 114 UBF | 0.5 | Pre-Sizing 7-day | 0.0 | 5.0 | 0.0 | 3.0 |
| myclobutanil | 50 | 3 sizing apps | | | | |
| BAS 114 UBF | 0.5% | Post-Sizing 7-day | | | | |
| Sulfur 80WP | 5600 | Pre-Sizing 7-day | 1.0 | 11.0 | 1.0 | 2.0 |
| myclobutanil | 50 | 3 sizing apps | | | | |
| Sulfur 80WP | 5600 | Post-Sizing 7-day | | | | |
| myclobutanil | 85 | 14-day | 0.0 | 2.0 | 0.0 | 12.0 |

[1]Disease ratings taken at 13 DALT for leaves and 23 DALT for berries

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process for making a biochemical agricultural product comprising the sequential steps of:
   (a) subjecting *Reynoutria sachalinensis* to organic solvent extraction;
   (b) concentrating the extract in a first stage concentration procedure;
   (c) adding a liquid nitrogen-containing stabilizer to the concentrated extract to form a stabilized mixture thereof; and then
   (d) concentrating the stabilized mixture to remove greater than 95 wt. % of organic solvent remaining therein.

2. The process of claim 1, wherein the organic solvent is ethanol.

3. The process of claim 1, wherein steps (a) and (c) include distillation to remove organic solvent.

4. The process of claim 3, wherein said distillation is accomplished under vacuum.

5. The process of claim 1, wherein step (d) includes distilling to remove a major portion of the remaining organic solvent.

6. The process of claim 1, wherein said *Reynoutria sachalinensis* is in a dried, particulate form.

7. The process of claim 1, wherein step (a) includes the steps of:
   (i) subjecting said *Reynoutria sachalinensis* to a primary organic solvent extraction to form a primary solvent extract,
   (ii) separating the primary solvent extract from said Reynoutria sachalinensis, and then
   (iii) subjecting said *Reynoutria sachalinensis* to a secondary organic solvent extraction to obtain a secondary solvent extract.

8. The process of claim 7, wherein the primary and secondary solvent extracts are combined and subjected to said first stage concentration according to step (b).

9. The process of claim 7, wherein said organic solvent in said primary and secondary organic solvent extractions is added to said *Reynoutria sachalinensis* in an amount of up to about 6 liters organic solvent per kilogram *Reynoutria sachalinensis* on a dry weight basis.

10. The process of claim 1, wherein said liquid stabilizer has a boiling point at least 10° C. greater than said organic solvent.

11. The process of claim 1, wherein the nitrogen-containing stabilizer comprises a fertilizer which includes at least one of urea, ammonium nitrate, calcium nitrate and magnesium chloride.

12. The process of claim 11, wherein the fertilizer is a salt solution containing urea and at least one of ammonium nitrate, calcium nitrate and magnesium chloride.

13. The process of claim 1 or 11, wherein said liquid stabilizer is added in an amount of at least about 0.25 liters per kilogram of the *Reynoutria sachalinensis* on a dry weight basis.

14. The process of claim 1 or 11, wherein said liquid stabilizer is added in an amount of at least about 0.50 liters per kilogram of the *Reynoutria sachalinensis* on a dry weight basis.

15. The process of claim 1, wherein step (b) is practiced so as to remove at least about 60 vol. % of the organic solvent.

16. A process for forming a stabilized biochemical agricultural product containing an organic solvent extract of *Reynoutria sachalinensis* comprising the steps of subjecting an organic solvent extract of dried particulate *Reynoutria sachalinensis* to first and second extract concentration stages, and prior to said second extract concentration stage, mixing the concentrated extract from said first extract concentration stage with a liquid fertilizer which is a salt solution containing urea and at least one of ammonium nitrate, calcium nitrate and magnesium chloride in an amount sufficient to allow removal of greater than 95 wt. % of the organic solvent during said second extract concentration stage.

17. The process of claim 16, wherein, prior to said first extract concentration stage, said dried particulate *Reynoutria sachalinensis* is subjected to primary and secondary solvent extractions to obtain primary and secondary solvent extracts which are combined prior to said first extract concentration stage.

18. The process of claim 17, wherein said first and second solvent extracts are separated from said *Reynoutria sachalinensis* by filtration.

19. The process of claim 16, wherein said liquid fertilizer is mixed with said concentrated extract from said first extract concentration stage in an amount of at least about 0.25 liters of fertilizer per kilogram of *Reynoutria sachalinensis* on a dry weight basis.

20. The process of claim 19, wherein said liquid fertilizer is mixed in an amount of at least about 0.50 liters of fertilizer per kilogram of *Reynoutria sachalinensis* on a dry weight basis.

21. The process of claim 16, wherein said organic solvent extract includes up to about 6 liters of organic solvent per kilogram of *Reynoutria sachalinensis* on a dry weight basis.

22. The process of claim 16, wherein said first extract concentration stage removes at least about 60 vol. % of the organic solvent.

23. The process of claim 16 or 22, wherein said second extract concentration stage is practiced such that no more than about 10 vol. % of the organic solvent remains.

* * * * *

UNITED STATES PATENT AND TRADEMARK OFFICE
CERTIFICATE OF CORRECTION

PATENT NO. : 5,989,429
DATED : November 23, 1999
INVENTOR(S) : Ted R. Bardinelli; David E. Mann; David G. Hobbs It is certified that error appears in the above-identified patent and that said Letters Patent is hereby corrected as shown below:

Column 1, line 53, change "inefficacy" to -efficacy-

Signed and Sealed this

Twenty-third Day of May, 2000

Attest:

Q. TODD DICKINSON

*Attesting Officer*  *Director of Patents and Trademarks*